US008227220B2

(12) United States Patent
Adhikari et al.

(10) Patent No.: US 8,227,220 B2
(45) Date of Patent: Jul. 24, 2012

(54) PROCESS FOR THE PREPARATION OF ETHANOL FROM STARCH

(75) Inventors: Dilip Adhikari, Uttranchal (IN); Tsering Stobdan, Uttranchal (IN); Ravindra Pal Singh, Uttranchal (IN); Ashok Kumar Gupta, Uttranchal (IN)

(73) Assignee: Council of Scientific & Industrial Research, New Delhi (IN)

(*) Notice: Subject to any disclaimer, the term of this patent is extended or adjusted under 35 U.S.C. 154(b) by 475 days.

(21) Appl. No.: 12/593,920

(22) PCT Filed: Mar. 26, 2008

(86) PCT No.: PCT/IN2008/000189
§ 371 (c)(1),
(2), (4) Date: Sep. 30, 2009

(87) PCT Pub. No.: WO2008/120233
PCT Pub. Date: Oct. 9, 2008

(65) Prior Publication Data
US 2010/0099156 A1 Apr. 22, 2010

(30) Foreign Application Priority Data
Mar. 30, 2007 (IN) .............................. 702/DEL/2007

(51) Int. Cl.
*C12P 7/06* (2006.01)
*C12P 39/00* (2006.01)
*C12P 7/14* (2006.01)
*C12P 1/04* (2006.01)
*C12P 1/02* (2006.01)
*C12P 1/00* (2006.01)

(52) U.S. Cl. ............ 435/161; 435/41; 435/42; 435/162; 435/170; 435/171

(58) Field of Classification Search .................. None
See application file for complete search history.

(56) References Cited

FOREIGN PATENT DOCUMENTS
WO WO 2005113785 A2 * 12/2005
WO 2006/117536 A 11/2006

OTHER PUBLICATIONS

Nazina et al. 2001. "Taxonomic study of aerobic thermophilic bacilli: descriptions of *Geobacillus subterraneus* gen.nov., sp.nov, . . . " International Journal of Systematic and Evolutionary Microbiology, 51, 433-446.*

M. Banat, P. Nigam and R. Marchant 1992. Isolation of thermotolerant, fermentative yeasts growing at 52 C and producing ethanol at 45 C and 50 C. World Journal of Microbiology and Biotechnology. vol. 8, No. 3, 259-263.*

Banat, I.M., Singh, D. and R. Marchant 1996. The Use of a Thermotolerant Fermentatitve *Kluyveromyces marxianus* IMB3 Yeast Strain for Ethanol Production. Acta Biotechnologia, vol. 2-3, pp. 215-223.*

Singh, D. P. Nigam, Banat, I.M., and R. Marchant 1998. Review: Ethanol production at elevated temperatures and alcohol concentrations: Part II—Use *Kluyveromyces marxianus* IMB3. World Journal of Microbiology and Biotechnology. vol. 14, pp. 823-834.*

Hughes, D. B. et al. 1984. The Effect of Temperature on the Kinetics of Ethanol Production by a Thermotolerant Strain of *Kluyveromyces marxianus*. Biotechnology Letters, vol. 6, No. 1, pp. 1-6.*

Duvnjak, D. et al., 1982. Production of Alcohol from Jerusalem Artichokes by Yeasts. Biotechnology and Bioengineering, vol. 34, pp. 2297-2308.*

Ward, C. et al. 1995. Production of ethanol at 45° C. on starch-containing media by mixed cultures of the thermotolerant, ethanol-producing yeast *Kluyveromyces marxianus* IMB3 and the thermophilic filamentous fungus *Talaromyces emersonii* CBS 814.70 Appl Microbiol. Biotechnology, vol. 42, pp. 408-411.*

Mark A. Payton. 1984. Production of ethanol by thermophilic bacteria. Trends in Biotechnology, vol. 2, No. 6, pp. 153-158.*

* cited by examiner

*Primary Examiner* — Jon P Weber
*Assistant Examiner* — Kailash C Srivastava
(74) *Attorney, Agent, or Firm* — Ladas & Parry LLP

(57) ABSTRACT

The present invention provides a process for the preparation of ethanol from starch. Specifically, the present invention provides a process for the preparation of ethanol from starch such as tapioca, potato, sweet sorghum, rice by liquification and saacharification of starch and subsequent fermentation of mono saccherides to ethanol in presence of thermophilic micro-organisms.

13 Claims, No Drawings

PROCESS FOR THE PREPARATION OF ETHANOL FROM STARCH

FIELD OF THE INVENTION

The present invention relates to a process for the preparation of ethanol from starch. More particularly, the present invention relates to a process for the preparation of ethanol from starch such as tapioca, potato, sweet sorghum, rice by liquification and saccharification of starch and subsequent fermentation of mono saccherides to ethanol in presence of thermophilic micro-organisms.

BACKGROUND OF THE INVENTION

Plant products such as tapioca, corn, rice, potato, sweet sorghum contain starch that used as feedstock for the production of ethanol. According to conventional process, starch containing agricultural products are grinded and made starch slurry or gelatinized with water for enzymatic hydrolysis. The starch slurry is cooked and liquefied by alpha amylase or liquefying enzyme at 95° C. and pH 6 for 2-3 hours. The liquefied slurry thus obtained is subjected for further hydrolysis to glucose by saccharifying enzyme, glucoamylase at lower temperature (40-60° C.) and pH 4.0 to 4.5 for 6 hrs. The glucose syrup thus obtained is then fermented using yeast, *Saccharomyces cerevisiae* at 30° C. and PH 4.0 to 4.5 for about 48 hrs. The fermented broth is then distilled at 75° C. to recover ethanol of 95% purity. The total time required for conversion of starch to ethanol in the fermentation broth in the conventional process is around 65 to 75 hrs.

Improvement in the efficiency of conventional process has been made by developing simultaneous saccharification and fermentation (SSF) process in which saccharifying enzyme can function under the same conditions of fermentation at 30° C. and pH 4.0 to 4.5. The process significantly saves time and energy during saccharification and fermentation process. However SSF process has the drawback on high energy input for liquefaction at 90° C. and ethanol recovery at 70° C. after fermentation at 30° C.

In the prior art such as described by Yamamoto et al. in U.S. Pat. No. 4,474,883 (1984) raw root stock starch is liquefied by bacterial amylase at 80-90° C. and pH 5.0. The resulting solution is hydrolyzed by glucoamylase and then fermented by yeast at 25 to 30° C.

In prior art Verma et al. 2000, Bioresource Technology, 72:261-266 reported bioconversion of starch to ethanol by coculturing *Saccharomyces diastaticus* and *Saccharomyces cerevisiae* in a single step process; the process was conducted at 30° C. and ethanol production decreased beyond 37° C. Therefore the process has the limitation of high input of energy for distillation of ethanol.

Bunni et al. in processing and quality of foods vol. 2, eds. Zeuthen P., Cheftel, J. C., Ericisson, C., Goemly, T. R., Linko, P., Paulus, K. pp 174-280, Elsevier Applied Pubs. Reported that the thermophilic fungus, I CBS 814.70 is capable of producing a relatively thermostable amylolytic enzymes at 45° C. on starch. Direct bioconversion of starch to ethanol using the co-culture of fungus *Talaromycea emersonii* CBS 814.70 and *Kluyoveramyces marxiamus* IMB3 at 45° C. was demonstrated by Ward et al. (Applied Microbiology and Biotechnology 43, pp 408-411) in which maximum ethanol concentration of 1.5% was reported in 40 hrs representing 70% of the theoretical yield.

Ethanol production at elevated temperature and alcohol concentration by using *Kluyoveromyces marxianus* IMB3 was reviewed by Singh et al. World Journal Microbiology 14, 823-834 (1998) in which they have reported mixed culture fermentation on starch containing media (4% w/v) capable of production 12 gl$^{-1}$ in 65 hrs at 45° C.

In the prior art methods, handling of starch is difficult at normal fermentation temperature (45° C.) due to high viscosity and gel forming tendency of starch. Liquefaction of starch is necessary before starch is saccharified and fermented. Time required for overall conversion of starch to ethanol was longer than 40 hrs. in the most prior art for ethanol production from starch was done by using two microorganisms used in two different steps operating at different conditions. The conventional process require high input of heat and agitation energy for liquification of starch slurry at 95° C.; cooling of the slurry is required to 40 to 60° C. for saccharification by glucoamylase at pH 6.5. Further cooling is required to 30° C. for fermentation by yeast *Saccharomyces cerevisiae*.

Therefore new enzymes that can simultaneously liquifying and saccharfying preferably at higher temperature e.g. above 40° C. is required so that hydrolysis can be carried out at a faster rate. Further fermentation of monosaccaharides obtained from starch hydrolysis can be carried out at faster rate by using thermophilic ethanologens.

OBJECTIVES OF THE INVENTION

The main object of the present invention is to provide a process for the preparation of ethanol from starch, at temperature above 45° C. using thermophilic microorganisms.

Another objective of the present invention is to provide thermostable composition of alpha amylase and glucoamylas, which is capable of liquifying and saccharifying starch simultaneously above 45° C.

Still another objective of the invention is to provide a thermophilic ethanologen capable of fermenting sugars produced by the enzymatic hydrolysis of starch to ethanol above 45° C.

SUMMARY OF THE INVENTION

Accordingly the present invention provides a process for the preparation of ethanol from starch using thermophilic microorganisms and the said process comprising the steps of:
 (a) cultivating, harvesting and preserving the thermophilic microorganism selected from *Geobacillus* sp. IIPTN (MTCC 5319) and ethanologen *Kluyoveromyces* sp. IIP E453 (MTCC 5314),
 (b) subjecting the starch to simultaneous liquification and saccharification by extra cellular enzymes of the bacteria *Geobacillus* sp. IIPTN (MTCC 5319), at temperature of 40-80° C., at pH in the range of 5-7.0, to obtain the starch hydrolysate,
 (c) subjecting the above said starch hydrolysate obtained in step (b) to fermentation to ethanol by thermophilic ethanologen *Kluyoveromyces* sp. IIP E453 (MTCC 5314), at a temperature in the range of 40-100° C., at a pH in the range of 4.5-5.5, followed by the recovery of ethanol by conventional distillation,
 OR
 (d) subjecting the starch to simultaneous liquification, saccharification and fermentation by co-culturing thermophilies, *Geobacillus* sp. IIPTN (MTCC 5319) and *Kluyoveromyces* sp. IIP E453 (MTCC 5314), at a temperature of 40-60° C. and at a pH of 4.5-5.5, followed by the recovery of ethanol by known method.

In an embodiment of the present invention the starch used is selected from the group consisting of cassava, potato, sweet potato, rice, wheat, corn and a mixture thereof.

In yet another embodiment the thermophilic bacteria *Geobacillus* sp. IIPTN (MTCC 5319) obtained step in (a) is cultivated in a medium M1 comprising sodium hydrogen phosphate 0.5-1 g per liter; magnesium chloride 0.1-0.5 g per liter; trace metals solution 20 ml per liter of M1 medium containing calcium, zinc, Iron, manganese, copper, nickel, molybdenum 2-5 ppm; Bacto trypton 6-12 g per liter; yeast extract 2-4 liter and starch 5-10 g dissolved per liter of distilled water, at pH in the range of 5.0-7.0 and the temperature in the range of 45-70° C.

In yet another embodiment the thermophilic ethanologen *Kluyoveromyces* sp. IIP E453 MTCC 5314) obtained in step (a) is cultivated in a bioreactor in the medium M2 comprising Ammonium sulphate 1-4 g per liter; sodium hydrogen phosphate 0.1-0.3 g per liter; potassium hydrogen phosphate 0.1-0.3 g per liter; yeast extract 0.5-2.0 g per liter and glucose 10-20 g per liter of distilled water, at pH in the range of 4-6 and at a temperature in the range of 40-60° C.

In yet another embodiment the cells of thermophillic micro organism obtained in step (a) are harvested by centrifugation at 8000 to 18000 rpm for 10 to 30 minutes and is preserved at −70 to −90° C. either separately or together as co culture.

In yet another embodiment the liquification and saccharification of starch in step (b) is carried out using the thermophilic microorganism *Geobacillus* sp. IIPTN (MTCC 5319) (Gene Bank accession No. DQ 323407) in the medium MI.

In yet another embodiment the fermentation of starch hydrolysate is carried out using thermophilic ethanologen *Kluyoveromyces* sp. IIP E453 (MTCC 5314) in the medium comprising ammonium sulphate 1-4 g per liter; sodium hydrogen phosphate 0.1-0.3 g per liter; potassium hydrogen phosphate 0.1-0.3 g per liter; yeast extract 0.5-2.0 g per liter of starch hydrolysate.

In yet another embodiment the fermentation of starch hydrolysate is carried out at temperature preferably in the range of 45-60° C.

In yet another embodiment the thermophilies *Geobacillus* sp. IIPTN (MTCC 5319) and *Kluyoveromyces* sp. IIP E453 (MTCC 5314) used in step (d) are co cultured in the medium comprising ammonium sulphate 1-4 g per liter; sodium hydrogen phosphate 0.1-0.3 g per liter; potassium hydrogen phosphate 0.1-0.3 g per liter; yeast extract 0.5-2.0 g per liter, citric acid 0.5-1 g per liter; trace metals solution 20 ml per liter containing calcium, zinc, iron, manganese, copper, nickel, molybdenum 2-5 ppm and Bacto trypton 2-5 g per liter and starch 1-5% in the distilled water.

In yet another embodiment the process is carried out either in batch mode using the microorganisms in liquid phase or in continuous mode using immobilized microorganisms, at a temperature in the range of 40-60° C.

In yet another embodiment the microorganisms *Geobacillus* sp. IIPTN (MTCC 5319) and *Kluyoveromyces* sp. HP E453 (MTCC 5314) are immobilized on heterogeneous support selected from the group consisting of cellulosic fibre, silk fibre, calcium aliginate gels, metal oxides or silicates and synthetic polymers and combinations thereof.

In still another embodiment the heterogeneous support used for the immobilization of microorganisms *Geobacillus* sp. IIPTN (MTCC 5319) and *Kluyoveromyces* sp. IIP E453 (MTCC 5314) is preferably cellulosic fibre.

DETAIL DESCRIPTION OF THE INVENTION

In the process of the present invention the liquifaction and saccharification of starch selected from the cassava tapioca, potato, sweet potato, rice, wheat or corn or mixtures thereof and fermentation of hydrolysate thus produced is carried out separately or simultaneously in a single step. The reaction can be carried out in batch mode using the microorganism in liquid phase or in continuous mode using immobilized microorganisms.

In one of the feature of the present invention the thermophilic bacteria *Geobacillus* sp. IIPTN is cultivated in the medium M1 consisting of sodium hydrogen phosphate 0.5-1 g per liter; magnesium chloride 0.1-0.5 g per liter; trace metals solution 20 ml per liter of M1 medium containing calcium, zinc, Iron, manganese, copper, nickel, molybdenum 2-5 ppm; Bacto trypton 6-12 g per liter; yeast extract 2-4 g per liter and starch 5-10 g dissolved per liter of distilled water. The pH of the medium is adjusted in the range of 5.0-7.0 and the temperature during the cell cultivation is maintained in the range of 45-70° C.

In yet another feature of the present invention the thermophilic ethanologen *Kluyoveromyces* sp. IIP E453 is cultivated in a bioreactor in the medium M2 prepared by dissolving of Ammonium sulphate 1-4 g per liter; sodium hydrogen phosphate 0.1-0.3 g per liter; potassium hydrogen phosphate 0.1-0.3 g per liter; yeast extract 0.5-2.0 g per liter and glucose 10-20 g per liter of distilled water. The pH of the medium is adjusted in the range of 4-6 and temperature and agitation at 300-400 rpm. in the range of 40-60° C., aeration 0.5-1 μm.

The harvesting of thermophilic microorganisms is carried out by centrifugation at 800-18000 rpm for 10-30 minutes and preserved at −70 to −90° C. either separately or as co-culture.

In the present invention the liquification and saccharification of starch is carried out using thermophilic microorganism *Geobacillus* sp. IIPTN (Gene Bank accession No. DQ 323407) in medium M1 at 40-100° C., preferably 40-80° C. in the pH range of 5-7 and agitation at 100-200 rpm. The fermentation of starch hydrolysate is carried out using thermophilic ethanologen *Kluyoveromyces* sp. IP E453 in the medium prepared by dissolving Ammonium sulphate 1-4 g per liter; sodium hydrogen phosphate 0.1-0.3 g per liter; potassium hydrogen phosphate 0.1-0.3 g per liter; yeast extract 0.5-2.0 g per liter of starch hydrolysate. The fermentation of starch hydrolysate is carried out at 40-100° C. preferably greater than 45° C. at pH in the range of 4.5-5.5.

In the present invention, alternatively the liquification, saccharification of starch to produce starch hydrolysate and its fermentation are carried out in single step at temperature in the range of 40-60° C. and pH in the range of 4.5-5.5. In this case the thermophilies *Geobacillus* sp. IIPTN and *Kluyoveromyces* sp. IIP E453 are used as co culture in the medium prepared by dissolving of Ammonium sulphate 1-4 g per liter; sodium hydrogen phosphate 0.1-0.3 g per liter; potassium hydrogen phosphate 0.1-0.3 g per liter; yeast extract 0.5-2.0 g per liter, citric acid 0.5-1 g per liter; trace metals solution 20 ml per liter containing calcium, zinc, iron, manganese, copper, nickel, molybdenum 2-5 ppm and Bacto trypton 2-5 g per liter and starch 1-5% in the distilled water.

In continuous mode operation, the process is carried out using immobilized microorganisms at 40-60° C. The microorganism *Geobacillus* sp. IIPTN and *Kluyoveromyces* sp. IIP E453 are immobilized on heterogeneous support selected from the group consisting of cellulosic fibre, silk fibre, calcium aliginate gels, metal oxides or silicates and synthetic polymers or combinations thereof, preferably cellulosic fibres. Ethanol produced is recovered by conventional distillation.

In the investigations it was found that in continuous mode operation using immobilized microorganisms the over all rate of liquification, saccharification and fermentation was more than 3 times faster than in liquid-phase batch mode.

It will be apparent from the foregoing that the present invention provides a process to produce ethanol from starch using thermophilic microorganisms in batch or continuous mode at higher temperature in the range of 40-60° C. to get higher rates of reaction and through put.

The thermophilic *Geobacillus* sp. IIPTN (MTCC 5319) and thermotolerant ethanologen *Kluyveromyces* sp. IIP E453 (MTCC 5314) required to practice the claimed invention are currently available from Microbial Type Culture Collection and Gene Bank (MTCC), Institute of Microbial Technology, Sector 39-A, Chandigarh-160036 (India).

Data Sheet of the thermophilic Strain
*Kluyoveromyces* IIP E453 (MTCC 5314)
Growth profile Date of deposition Oct 27, 2006

| | | |
|---|---|---|
| 1. Microroganism: | | Yeast |
| 2. Name: | | *Kluyoveromyces* sp. IIP E453 (MTCC 5314) |
| 3. Morphology: | Cell> | Large oval, budding, Gram + ve |
| | Colony> | Small, round, hemispherical surface, cream color. |
| 4. Growth Temperature: | | 37° C.-50° C. |
| 5. Growth cycle: | | 30 h, lag phase ~4 h |
| 6. pH: | | 4.0-6.5 |
| 7. Specific growth rate on glucose: | | 0.55h$^{-1}$ |
| 8. Yield on glucose: | | 0.22 |
| 9. Yield on xylose: | | 0.24 |
| 10. Carbohydrate utilization: | | |
| | | a) Glucose |
| | | b) Xylose |
| | | c) Sucrose |
| | | d) Maltose |
| | | e) Galactose |
| | | f) Cellobioes |
| Fermentation profile | | |
| 1. Temperature: | | 45° C.-50° C. |
| 2. pH: | | 3.0-6.5 |
| 3. Sugar substrates: | | a) Glucose |
| | | b) Maltose |
| | | c) Sucrose |
| | | d) Galactose |
| Carbohydrate: | | a) Starch |
| 4. Mode of fermentation process: | | |
| | | a) Batch  50 h |
| | | b) Continuous  100 h immobilized bioreactor, |
| | | c) Fed batch  60 h |
| 5. Volume of fermentation: temp., | | 2.0I & 5.0I fermentor (Model NBS) with pH, DO, agitation control facilities. Exhaust gas (CO$_2$, O$_2$, H$_2$) analyser. |
| 6. Yield of ethanol, g/g: | | Glucose ~46% (~90% of Theoretical yield) |
| 7. Productivity, g.l$^{-1}$.h$^{-1}$: | | 14 g.l$^{-1}$.h$^{-1}$ (continuous) |
| 8. Ethanol tolerance: | | 5% |

Data Sheet at the thermophilic Strain
*Geobacillus sp.* IIPTN (MTCC 5319)
Growth profile. Date of deposition Jan. 24, 2007

| | | |
|---|---|---|
| 1. Microorganism: | | Bacteria |
| 2. Name: | | *Geobacillus sp.* IIPTN (MTCC 5319) |
| 3. Gene Bank Accen No: | | DQ 323407 |
| 4. Morphology: | Cell> | bacillus, Gram + ve |
| | Colony> | irregular, flat surface, cream color. |
| 5. Growth Temperature: | | 50° C.-80° C. |
| 6. Growth cycle: | | 24 h, lag phase ~4 h |
| 7. pH: | | 5.5-7.0 |
| 8. Specific growth rate on glucose: | | 0.55h$^{-1}$ |
| 9. Yield on glucose: | | 0.42 |
| 10. Carbohydrate utilization: | | |
| A) Starch: | | 1) potato soluble, 2) Cassava roots, 3) processed Tapioca, 4) wheat flour, 5) corn flour |
| B) Glucose | | |
| C) Cellulose: | | CMC, Micro crystaline |
| D) Maltose | | |
| E) Galactose | | |
| F) Cellobioes | | |
| Starch hydrolysis | | |
| 1. Temperature: | | 60° C.-100° C. |
| 2. pH: | | 4.0-9.0 |
| 3. Enzymes produced: | | a) Glucoamylase |
| | | b) α-amylase |
| | | c) β-glucosidase |

The following examples are given by the way of illustration and therefore should not be construed to limit the scope of the invention.

EXAMPLE-1

Cultivation of *Geobacillus* sp. IIPTN was cultivated in a batch bioreactor of a lit. capacity containing 500 ml growth medium designated as M1 constituting sodium hydrogen phosphate 1 g; ammonium chloride 3 g; potassium chloride 1 g; sodium sulphate 1 g; citric acid 1 g; magnesium chloride 1 g; trace elements (zinc, copper, iron, cobalt) 0.1 mg; trypton 1 g and glucose 10 g per liter. The cell culture was conducted at 50° C., pH 6 agitation 300 rpm and the aeration at 0.5 vvm for 25 hours. The bacterial cells were harvested by centrifugation at 8000 rpm for 15 minutes and preserved at −80° C. for further use.

EXAMPLE-2

Cultivation of *Kluyoveromyces* sp. IIP E453 (MTCC 5314) in a bioreactor of 2 lit. capacity containing 500 ml growth medium, designated as M2 constituting disodium hydrogen orthophosphate 0.1 g; sodium dihydrogen orthophosphate 0.2 g; ammonium sulphate 2 g; yeast extract 1.5 g; glucose 20 g per liter, pH 4.5. The yeast cells were cultivated at 40° C. with aeration at 0.5 vvm and agitation at 400 rpm for 26 hours. When the dry cell weight concentration reached 8.0 g/l. the yeast cells were harvested by centrifugation at 6000 rpm for 10 minutes and preserved at −80° C. for further use.

EXAMPLE-3

Simultaneous Liquifatiction and Saccharification of Starch

Hydrolysis of starch was done in a one liter flask containing 300 ml M1 medium except glucose was replaced with starch 10 g/l and cells of *Geobacillus* sp. IIPTM was added 5 g/l at 50° C., pH 7, 150 rpm for 5 hrs. Extracellular thermostable liquefying enzymes, α amylase and saccharifying enzyme, glucoamylase was produced by the bacterial cells and the enzymes hydrolyzed starch to fermentable sugar, glucose simultaneously. Hydrolyzed solution is centrifuged at 6000 rpm for 15 minutes.

EXAMPLE-4

Fermentation of Starch Hydrolysate

Fermentation of starch hydrolysate (200 ml) was conducted with a 50 ml of yeast cell suspension (5 g/l) in M2 medium with glucose equivalent of 40 g/l in a 500 ml jacketed glass vessel fitted with condenser and gas scrubber in series. Hot water 60° C. was circulated through the jacket by connecting the vessel with constant temperature water circulating bath. The condenser was connected to another circulating water bath maintained at 10° C. Anaerobic condition of the culture was maintained at the beginning of fermentation process by flushing of nitrogen gas through the jacketed vessel. A magnetic stirrer provided agitation in the vessel. Ethanol concentration in the fermented broth was measured by standard method during the fermentation period of 48 hrs. Maximum ethanol concentration of 1.8% in the fermentation broth was obtained within 40 hrs. Ethanol was produced 90% of theoretical yield based on reducing sugar, which was present in the starch-hydrolyzed stream. Ethanol (95% purity) was recovered from the fermented broth by distillation.

EXAMPLE-5

Simultaneous Liquifaction, Saccharification and Fermentation of Starch

Simultaneous liquifaction, saccharification and fermentation of starch to ethanol was done by co-culture of *Geobacillus* sp IIPTM (5 g/l) and *Kluyoveromyces* sp. IIP E453 (5 g/l) in medium M1 except glucose, containing starch 40 g/l at pH 5.5 and temperature 50° C. The process was carried out for 48 hrs in a jacketed vessel with condenser and gas scrubber in series and the temperature of the jacketed vessel and the condenser were maintained in the same way as described in example 4. Ethanol concentration in the fermented broth was measured at 6 hrs intervals for 48 hrs by standard method. The jacketed vessel was kept on a magnetic stirrer for providing agitation in the vessel.

The overall yield of ethanol was obtained 80% (W/V) of starch added in the medium with ethanol concentration of 1.8% within 30 hrs. Ethanol (95%) purity was obtained by distillation.

EXAMPLE-6

Fermentation of hydrolyzed starch was done as mentioned in example-4 except the temperature was increased to 55° C. and ethanol concentration of 1.8% was obtained within 30 hrs in comparison that of obtained at 40 hrs as mentioned in example-4.

EXAMPLE-7

Fermentation of hydrolyzed starch was done as mentioned in example-4 except the temperature was decreased to 45° C. and ethanol concentration of 1.8% was obtained within 46 hrs in comparison to that of obtained at 30 hrs as mentioned in example-6.

EXAMPLE-8

Simultaneous liquifaction, saccharification and fermentation of the starch was done as mentioned in example-5 except at 60° C. and ethanol concentration of 1.8% was obtained within 22 hrs in comparison to that of obtained at 30 hrs as mentioned in example-5.

EXAMPLE-9

Fermentation of the supernatant (200 ml) was conducted with immobilized yeast cell on solid support such as natural cellulosic or silk matters, synthetic fibers or metal oxides or alumina silicates which was packed in 70 ml in a jacketed glass column having length 80 cm and internal diameter 1 cm fitted with condenser and gas scrubber in series. Hot water 60° C. was circulated through the jacket by connecting the column with constant temperature water circulating bath. The condenser was connected to another circulating water bath maintained at 10° C. The supernatant containing fermentable sugars was pumped through the column at 30 ml per hr and the outlet stream was collected in vessel. Ethanol concentration in the fermented broth was measured by standard method during the fermentation period of 48 hrs. Maximum ethanol concentration of 2% in fermentation broth was obtained under the specified operating conditions within 8 hrs. Ethanol was produced 93% of theoretical yield based on reducing sugar, which was present in the starch-hydrolyzed stream. Ethanol (95% purity) was recovered from the fermented broth by distillation. The productivity of ethanol was obtained 13 $g^{-1}.l^{-1}$ as compared to 1.0 $g^{-1}.l^{-1}$ obtained in batch fermentation process given in example-4.

ADVANTAGES OF THE INVENTION a) The process has the advantage of operating at a temperature which accomplishes liquification, saccharification and fermentation to convert starch biomass to ethanol by using the thermophilic microorganisms.
b) The process would save significant amount of energy input for bioethanol production as compared to hitherto known process.
c) The process has no risk of contamination by unwanted bacteria as it may occur in hitherto known process.
d) Cost of ethanol production would be lower.
e) The overall productivity of ethanol from starch biomass would be higher than known processes.

We claim:
1. A process for the preparation of ethanol from starch using thermophilic and thermotolerant microorganisms, said process comprising the steps of:
(a) cultivating, harvesting and preserving the thermophilic microorganism *Geobacillus* sp. IIPTN (MTCC 5319) and thermotolerant ethanologen *Kluyveromyces* sp. IIP E453 (MTCC 5314);
(b) subjecting the starch to simultaneous liquefaction and saccharification by extracellular enzymes of the bacteria *Geobacillus* sp. IIPTN (MTCC 5319), at temperature of 40° C.-80° C., at pH in the range of 5-7.0, to obtain the starch hydrolysate;
(c) subjecting said starch hydrolysate obtained in step (b) to fermentation to ethanol by thermotolerant ethanologen *Kluyveromyces* sp. IIP E453 (MTCC 5314), at a temperature in the range of 40° C.-100° C., at a pH in the range of 4.5-5.5, followed by the recovery of ethanol by conventional distillation; OR
(d) subjecting the starch to simultaneous liquefaction, saccharification and fermentation by co-culturing thermophile *Geobacillus* sp. IIPTN (MTCC 5319) and *Kluyveromyces* sp. IIP E453 (MTCC 5314) at a tempera- ture of 40° C.-60° C. and at a pH of 4.5-5.5, followed by the recovery of ethanol by known method.

2. A process according to claim 1, wherein the starch used is selected from the group consisting of cassava, potato, sweet potato, rice, wheat, corn and a mixtures thereof.

3. A process according to claim 1, wherein the thermophilic bacteria *Geobacillus* sp. IIPTN (MTCC 5319) obtained in step (a) is cultivated in a medium M1 comprising sodium hydrogen phosphate 0.5-1 g per liter; magnesium chloride 0.1-0.5 g per liter; trace metals solution 20 ml per liter of M1 medium containing calcium, zinc, iron, manganese, copper, nickel, molybdenum 2-5 ppm; tryptone 6-12 g per liter; yeast extract 2-4 g per liter and starch 5-10 g dissolved per liter of distilled water, at pH in the range of 5.0-7.0 and the temperature in the range of 45° C.-70° C.

4. A process according to claim 1, wherein the thermotolerant ethanologen *Kluyveromyces* sp. IIP E453 (MTCC 5314) obtained in step (a) is cultivated in a bioreactor in the medium M2 comprising ammonium sulphate 1-4 g per liter; sodium hydrogen phosphate 0.1-0.3 g per liter; potassium hydrogen phosphate 0.1-0.3 g per liter; yeast extract 0.5-2.0 g per liter and glucose 10-20 g per liter of distilled water, at pH in the range of 4-6 and at a temperature in the range of 40° C.-60° C.

5. A process according to claim 1, wherein the cells of thermophilic and thermotolerant microorganisms obtained in step (a) are harvested by centrifugation at 8,000 to 18,000 rpm for 10 to 30 minutes and is preserved at −70° C. to −90° C. either separately or together as co-culture.

6. A process according to claim 1, wherein the liquefaction and saccharification of starch in step (b) is carried out using the thermophilic microorganism *Geobacillus* sp. IIPTN (MTCC 5319) (Gene Bank accession No. DQ 323407) in the medium M1.

7. A process according to claim 1, wherein the fermentation of starch hydrolysate is carried out using thermotolerant ethanologen *Kluyveromyces* sp. IIP E453 (MTCC 5314) in the medium comprising ammonium sulphate 1-4 g per liter; sodium hydrogen phosphate 0.1-0.3 g per liter; potassium hydrogen phosphate 0.1-0.3 g per liter; yeast extract 0.5-2.0 g per liter of starch hydrolysate.

8. A process claimed in claim 1, wherein the fermentation of starch hydrolysate is carried out at temperature preferably in the range of 45° C.-60° C.

9. A process according to claim 1, wherein the thermophile *Geobacillus* sp. IIPTN (MTCC 5319) and thermotolerant ethanologen *Kluyveromyces* sp. IIP E453 (MTCC 5314) used in step (d) are co-cultured in the medium comprising ammonium sulphate 1-4 g per liter; sodium hydrogen phosphate 0.1-0.3 g per liter; potassium hydrogen phosphate 0.1-0.3 g per liter; yeast extract 0.5-2.0 g per liter, citric acid 0.5-1 g per liter; trace metals solution 20 ml per liter containing calcium, zinc, iron, manganese, copper, nickel, molybdenum 2-5 ppm and tryptone 2-5 g per liter and starch 1-5% in distilled water.

10. A process according to claim 1, is carried out either in batch mode using the microorganisms in liquid phase or in continuous mode using immobilized microorganisms, at a temperature in the range of 40° C.-60° C.

11. A process according to claim 10, wherein the microorganisms *Geobacillus* sp. IIPTN (MTCC 5319) and *Kluyveromyces* sp. IIP E453 (MTCC 5314) are immobilized on heterogeneous support selected from the group consisting of cellulosic fibre, silk fibre, calcium alginate gels, metal oxides or silicates and synthetic polymers and combinations thereof.

12. A process according to claim 11, wherein the heterogeneous support used for the immobilization of microorganisms *Geobacillus* sp. IIPTN (MTCC 5319) and *Kluyveromyces* sp. IIP E453 (MTCC 5314) is cellulosic fibre.

13. A process for producing ethanol which comprises fermenting starch with *Kluyveromyces* sp IIP E543 (MTCC 5314) either after or simultaneously with heating said starch with *Geobacillus* sp IIPTN (MTCC 5319) at a temperature of at least 40° C.

* * * * *